(12) United States Patent
Chladek

(10) Patent No.: US 8,892,213 B2
(45) Date of Patent: Nov. 18, 2014

(54) ORTHOTIC FEEDBACK SYSTEM

(71) Applicant: Noel Chladek, Des Moines, IA (US)

(72) Inventor: Noel Chladek, Des Moines, IA (US)

( * ) Notice: Subject to any disclaimer, the term of this patent is extended or adjusted under 35 U.S.C. 154(b) by 122 days.

(21) Appl. No.: 13/664,111

(22) Filed: Oct. 30, 2012

(65) Prior Publication Data

US 2014/0121574 A1   May 1, 2014

(51) Int. Cl.
*A61N 1/00* (2006.01)
*A61H 3/00* (2006.01)

(52) U.S. Cl.
CPC ....................................... *A61H 3/00* (2013.01)
USPC ........................................................ 607/115

(58) Field of Classification Search
USPC ........................................................ 607/115
See application file for complete search history.

(56) References Cited

U.S. PATENT DOCUMENTS

| | | | |
|---|---|---|---|
| 7,367,958 B2 | 5/2008 | McBean et al. | |
| 2001/0035723 A1* | 11/2001 | Pelrine et al. | 318/116 |
| 2007/0208392 A1* | 9/2007 | Kuschner et al. | 607/48 |
| 2011/0137375 A1* | 6/2011 | McBride | 607/49 |
| 2013/0123568 A1* | 5/2013 | Hamilton et al. | 600/13 |

OTHER PUBLICATIONS

Dynamic Response/Energy Storing AFO, Phatbraces.com. Printout of webpage. Noel J. Chladek.

* cited by examiner

*Primary Examiner* — Robert N Wieland
(74) *Attorney, Agent, or Firm* — Brett J. Trout, P.C.

(57) ABSTRACT

An orthotic feedback system for facilitating ambulation of a user requiring assistance in the joint motion of the ankle and foot. An energy-storing and energy-returning orthosis is coupled to the leg and foot of a user. Force sensors are positioned under the plantar surface of the heel and metatarsals of the foot. The sensors are coupled to a main control unit that sends signals to transcutaneous electrode pads coupled to the user's leg. The main control unit receives signals from the force sensors and sends signals to the transcutaneous electrode pads to cause plantar flexion and dorsiflexion of the user's foot during ambulation, to train the user's muscles to fire at the appropriate time and retrain the user to walk with a more normal gait.

15 Claims, 9 Drawing Sheets

ORTHOTIC FEEDBACK SYSTEM

TECHNICAL FIELD

The following disclosure relates generally to orthotic devices and, more particularly, to energy-storing and feedback orthotic devices.

BACKGROUND

Orthotic devices are well known in the art. When a user loses partial or complete control of a muscle group, orthotic devices compensate for some or all of the missing function. When used for rehabilitation of a user having weak or absent anterior and/or posterior calf muscle group function, prior art orthotic devices may provide the user's leg with support and alignment of the user's foot and ankle as the user walks or stands.

One drawback associated with prior art orthotic devices is that they limit the motion of the joints, thereby preventing the user's foot from moving through a full or normal range of motion during ambulation. An additional drawback associated with such prior art devices is that by limiting motion of the joints, prior art orthotic devices inhibit the use of electronic stimulation of the user's muscle groups to facilitate the user moving their foot through a full range of motion. Another drawback associated with such prior art orthotic devices is that by limiting the motion of the joints, such prior art devices lead to disuse atrophy. Still another drawback associated with such prior art devices is that they maintain the user's foot in a misaligned position during ambulation. This misalignment may cause electronic stimulation of the user's muscle groups to be ineffective in assisting propulsion. It would be desirable to provide an orthotic device that held a user's foot in proper alignment, through an increased range of motion. It would also be desirable to provide an orthotic device that could be used in association with electronic stimulation of the user's muscle groups to facilitate the user moving their foot through a full range of motion.

It is known in the art to provide an orthotic device with a resilient component that stores energy as the user steps down on the device, and which returns that energy to the user's foot as the user lifts the foot off of the ground. The resiliency of such prior art devices replaces force missing from a user's missing or compromised leg muscles. Such resilient orthoses also allow a users foot to move through a wider, more normal, range of motion. One drawback associated with such prior art orthoses is that they do not stimulate the user's legs, to retrain the muscle firing of the legs to walk in a more normal gait. It would be desirable to provide a resilient orthotic device that could be used in association with electronic stimulation of the user's muscle groups to retrain the legs to walk in a more normal gait.

It is also known in the art to provide devices that electronically stimulate a user's muscle groups. Such devices apply electricity transcutaneously to anterior and/or posterior calf muscle groups to facilitate walking and standing. Generally, these devices are applied to stimulate the anterior calf muscle group, effecting toe pick up during the swing phase of a user's gait. Anterior calf group firing can be effected with electronic stimulus in the absence of an orthosis. Electrical stimulus of the posterior calf muscle group can retrain firing patterns for propulsion during the weight-bearing phase of walking. As the electrical stimulus is merely a trigger to get the user to actually fire the muscle, electrical stimulus is not optimal for training the user's posterior calf muscles to fire. Every electrical stimulus does not translate into the user actually firing the muscle. Electrical stimulus is simply too inconsistent to fire a user's posterior calf muscles sufficiently to allow for increasing propulsive speed with confidence of accident-free ambulation. Even if electrical stimulus was capable of getting the user to fire posterior calf muscles ninety percent of the time, the one time the electrical stimulus failed to get the user to fire the posterior calf muscles, the user would trip and likely fall. It would, therefore, be desirable to provide a system for electrically stimulating a user to fire posterior calf muscles without causing the user to stumble or fall.

Prior art electronic stimulation devices assist users in retraining muscle groups to fire at the appropriate time. Such devices often use the position of one leg relative to the other leg to trigger the firing of the appropriate muscle group in the leg needing assistance. While electronic stimulation devices have been shown to assist in the rehabilitation of users having weak or absent calf muscle group functions, such prior art devices also have drawbacks. One drawback associated with prior art electronic stimulation devices is in users who have developed misalignment of the joints. Electronic stimulation of posterior calf muscle function is less effective if the ankle and foot are not in proper alignment with the knee joint when electronic stimulation is applied to the calf muscle group.

Stimulation of the posterior calf muscle group while the joints are misaligned, would be of little or no effect at creating a function increase to propulsion during ambulation. If the foot is not in alignment, the propulsion from firing the muscle is ineffective at enabling the user to lengthen their step or increase their speed. This instability may also cause the user to shorten the stride of the pathological leg. Shortening the stride of the pathological leg throws off the timing of the electronic stimulus, further exacerbating instability. It would, therefore, be desirable to overcome the drawbacks associated with prior art devices and provide a resilient type orthosis which allowed for an extended range of motion for weakened or absent anterior and posterior calf muscle group function, while maintaining proper alignment of the calf and foot during rehabilitation. It would also be desirable to provide an orthosis that consistently created propulsion, retrained muscle firing patterns and increased the stability of the user's foot while standing and walking.

The difficulties encountered in the prior art discussed hereinabove are substantially eliminated by the present invention.

SUMMARY OF THE DISCLOSED SUBJECT MATTER

In accordance with the present invention, a resilient, energy-storing and feedback orthotic device is provided, having an orthosis that includes a calf section coupled to a foot section. A first gait position sensor and second gait position sensor are coupled to the foot section. A control unit is coupled to the gait position sensor. The control unit is also coupled to a first muscle stimulator and a second muscle stimulator.

In one embodiment of the device, the control unit and muscle stimulators are coupled to the calf section. The control unit may adjust the firing of the muscle stimulators in response to feedback received from the gait position sensors. The orthotic device is secured to a user's leg and foot. The control unit uses feedback from the first gait position sensor and second gait position sensor to trigger the firing of the first muscle stimulator and second muscle stimulator, to aid in standing and ambulation.

Within this combination, the resilient orthosis aligns the foot and replaces the absent propulsion forces, allowing the patient to increase their walking speed to normal. While maintaining stability and security. While at speed and in alignment, the electrical stimulation becomes more effective at retraining propulsive muscle firing. The Electrical stimulus also is able to retrain muscle firing at variable cadences.

BRIEF DESCRIPTION OF THE DRAWINGS

The present invention will now be described, by way of example, with reference to the accompanying drawings in which.

DETAILED DESCRIPTION OF THE DRAWINGS

Overview

An energy-storing and feedback orthotic system for facilitating leg and foot support, and motivation for users displaying weak or absent calf muscle strength. Weak or absent calf muscle group strength in a patient can lead to breakdown of the ankle ligamentous support structure as secondary muscles work to compensate for the weakness. The compensation of these secondary muscles, and the forces that pass through the foot during ambulation, combine to break down the ligamentous structure of the ankle and foot. Ligamentous structure breakdown can lead to misalignment of the user's foot during ambulation. Firing the user's anterior and posterior calf group muscles, without correctly aligning the foot, decreases the effectiveness of the foot as a lever to propel the user. If the anterior calf group muscles are not fired effectively, the user may be forced to raise the leg higher during swing through phase of ambulation to clear a still downward pointing toe. This alteration in gait raises energy consumption and forces the patient to slow their speed.

Through the swing phase of the ambulation stroke, a downward pointing toe that contacts the ground, may trip the patient or cause instability, forcing the user to slow cadence and shorten the time spent on the weaker foot and leg. Misalignment of the foot, altered cadence, and uneven time spent on each foot, may cause pain and may exacerbate deficiencies already associated with the leg and foot. Misalignment of the foot also may prolong the time required to properly retrain the user's anterior and posterior calf group muscles to fire properly on their own.

The orthotic feedback system combines force feedback sensors with electrical muscle stimulus and an energy storing orthotic device. The system maintains the user's foot in proper alignment, and properly fires anterior and posterior calf muscle groups, increasing stability and facilitating a more normal gait pattern. As the user moves, the electrical stimulation of the orthotic feedback system retrains muscle firing in correct cadence and keeps the foot properly aligned, to facilitate proper rehabilitation of the user's leg and foot. The orthotic feedback system's reinforcement of proper leg and foot function may encourage higher outcomes with rehabilitation and may reduce recovery time.

The energy-storing nature of the orthosis system of the present invention manually replaces the propulsive forces of the weak or absent calf group muscles, while maintaining alignment and stability of the foot and ankle. The orthosis is of a construction designed to store energy during the compression phase of ambulation, and return the stored energy to the user's leg during the extension phase of ambulation. The energy-storing nature of the orthosis also facilitates functional ambulation, with consistent increase of speed, variable step length and stable alignment. The electrical stimulus nature of the orthosis system of the present invention retrains the firing patterns of the user's posterior and/or anterior calf muscle groups. The electrical stimulus becomes more effective at retraining because if the stimulus fails to trigger the patient firing the muscle on a particular step, the orthosis is there to manually support the patient. Thus the patient can maintain increased cadence, allowing stable, continuous training at variable speeds of ambulation.

Figure 1:
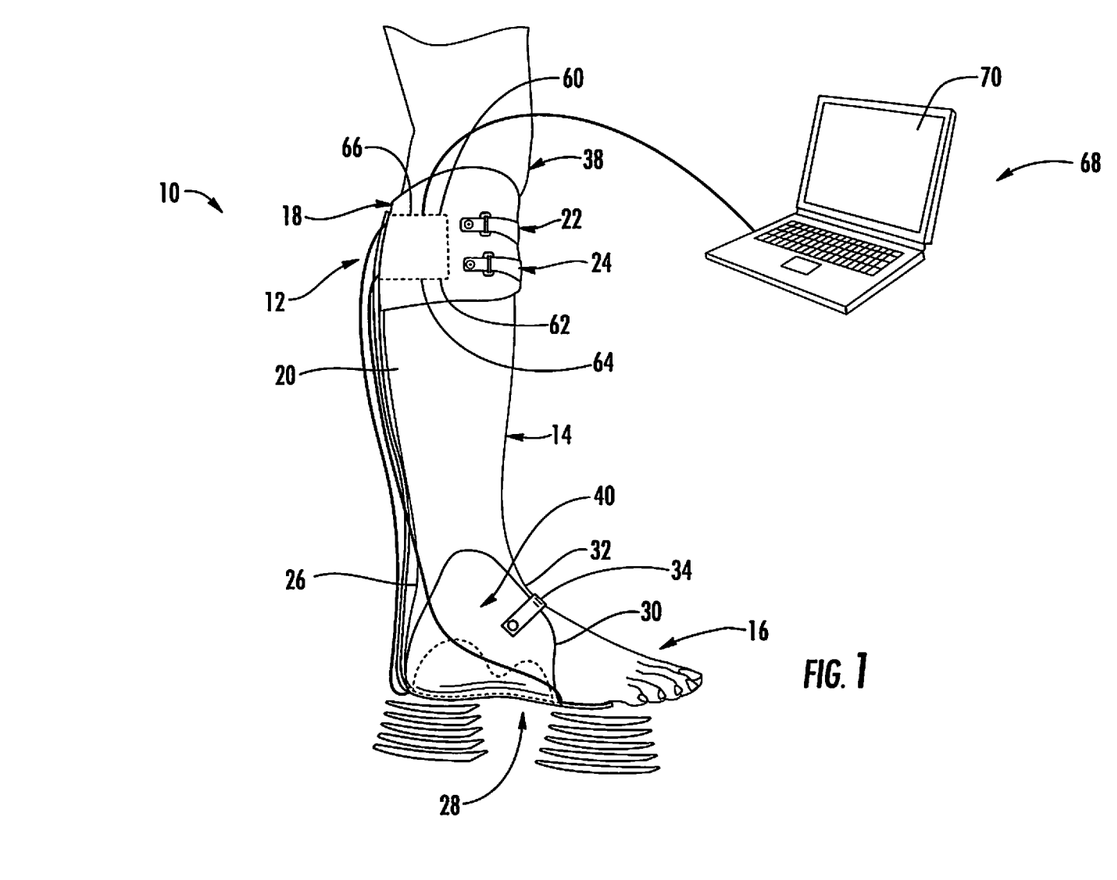
FIG. 1 is a side elevation of the orthotic feedback system of the present invention attached to a user's foot and leg.
Figure 2:
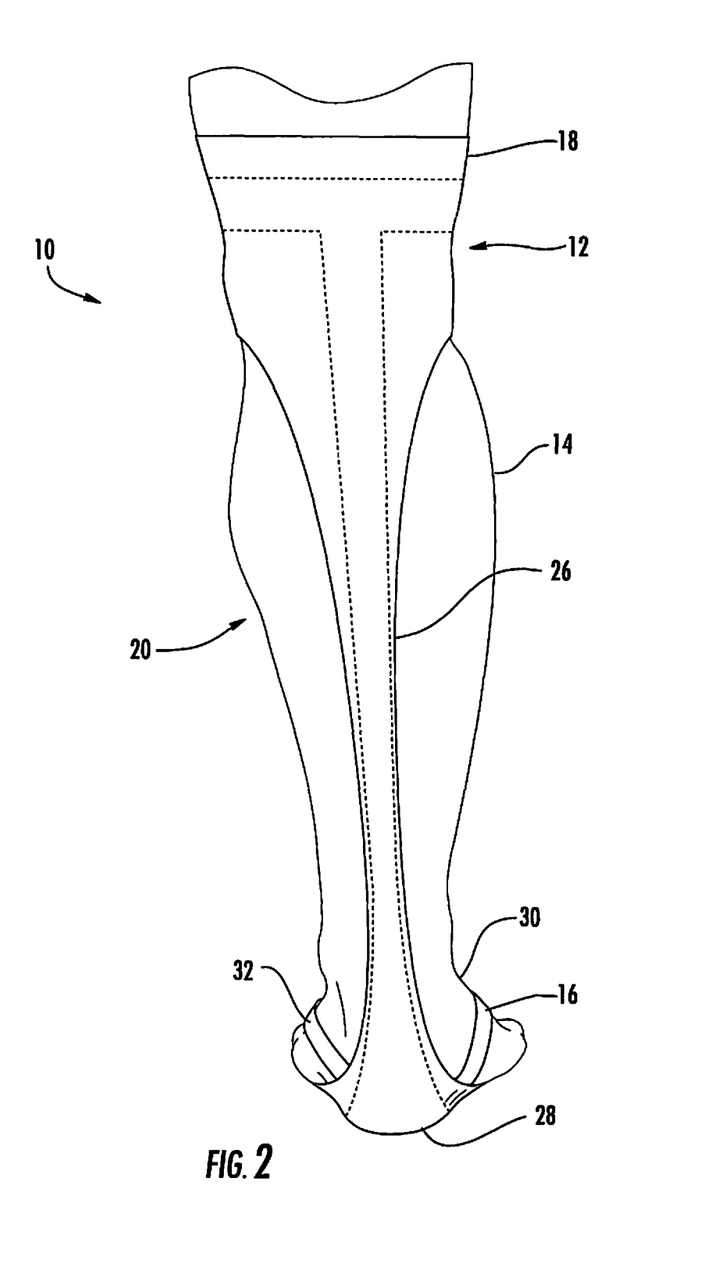
FIG. 2 is a rear elevation of the orthotic feedback system of FIG. 1.
Figure 3:
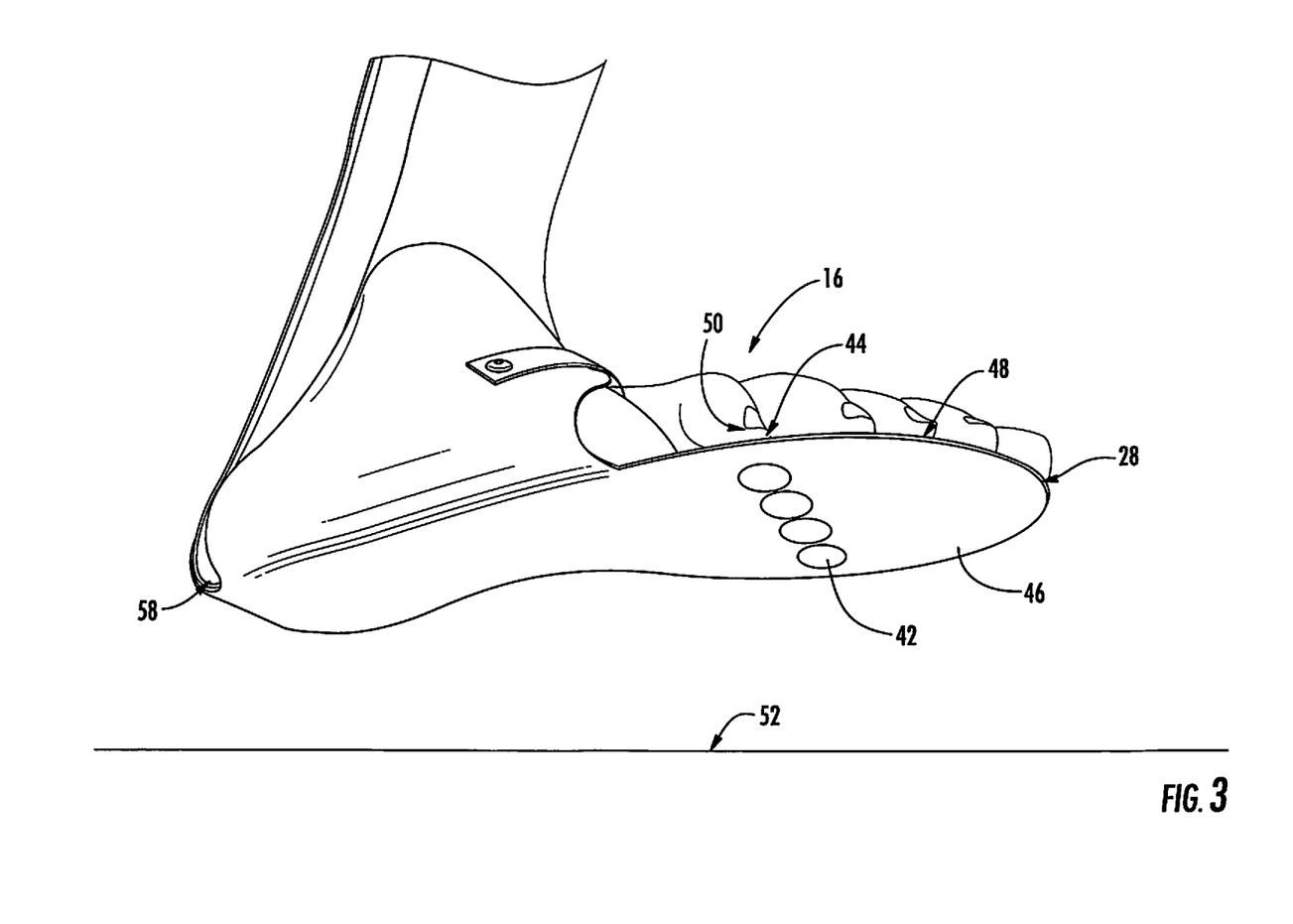
FIG. 3 is a bottom perspective view in partial phantom of the orthotic feedback system of FIG. 1.

FIG. 1 shows the orthotic feedback system (10). An orthosis (12) is provided on the user's leg (14) and foot (16). While the orthosis (12) may be of any type known in the art, in the preferred embodiment the orthosis (12) is a composite orthosis, such as that manufactured by Bio-Mechanical Composites, Inc. of Des Moines, Iowa. The orthosis (12) has a calf cuff (18) surrounding the user's calf (20) and secured thereto by hook and latch material straps (22) and (24) secured to the calf cuff (18). (FIGS. 1-3). Integrally molded to the calf cuff (18) is a calf section, which is preferably a resilient posterior support strut (26). The support strut (26) is integrally molded with a foot section, which is preferably a foot plate (28). The support strut (26) and foot plate (28) are preferably manufactured of a composite material, having a resiliency customized to match the missing weakened muscle forces. The resiliency also biases the alignment of the foot in the direction of the knee. The user's foot (16) rests on the foot plate (28) and is secured thereto by a pair of wings (30) and (32), integrally molded to the foot plate (28). The wings (30) and (32) are secured to the foot (16) by a hook and latch material strap (34).

While the orthosis (12) may be constructed of any suitable material, in the preferred embodiment the orthosis (12) is constructed of an internal carbon structure reinforced with an epoxy polymer. The orthosis (12) is preferably custom fit to the user's leg (14) and foot (16), so the center of the user's knee (38) is vertically aligned over the center of the user's ankle complex (40). The internal carbon structure and reinforced epoxy polymer is constructed to provide a resistance force and return of stored energy suitable to optimize the orthosis (12) for the levels of weakness experienced by the user, and to maintain proper alignment of the foot (16) relative to the leg (14).

As shown in FIGS. 2 and 3, a first gait position sensor, which in the preferred embodiment, is a first force sensor (42), is located on the underside of the foot plate (28) below the metatarsal area (44), or ball of the foot plate (28). The force sensor (42) is preferably a flexible piezoelectric force sensor, such as those well-known in the art to sense varying degrees of pressure. The first gait position sensor may, of course, be any suitable sensor known in the art, capable of detecting a pressure placed on the sensor. Alternatively, the first gait position sensor may be a mercury switch or opposing leg position detector, such as those known in the art. The force sensor (42) is preferably secured to the underside (46) of the foot plate (28) but may be positioned on the top side (48) of the foot plate (28). If desired, the force sensor (42) may be integrally molded within the foot plate (28). Securing the force sensor (42) to the underside (46) of the foot plate (28), allows the force sensor (42) to detect when the metatarsal (50) of the foot (16) is pressing against the ground (52), but to avoid a false positive detection when the metatarsal (50) of the foot (16) is pressing against the foot plate (28), when the foot plate (28) is not pressed against the ground (52).

Positioned on the top side (48) of the foot plate (28) over the plantar surface (54) or heel of the foot plate (28) is a second gait position sensor, which in the preferred embodiment is a second force sensor (56) of similar construction to the first force sensor (42). (FIGS. 2 and 3). The force sensors (42) and (56) are preferably between about 20 and 40 millimeters wide, between about 20 and 40 millimeters long, and between about 1 an 2 millimeters deep. The force sensors (42) and (56) are preferably flexible and between about 0.3 and 1.0 grams. Preferably, the force sensors (42) and (56) detect force application applied to various areas of the force sensors, and are constructed in a manner to detect the magnitude of the pressure applied across the range of about 30 to 800 newtons. The force sensor (56) is preferably positioned on the top side (48) of the foot plate (28) as the plantar surface (58), or heel of the foot (16), is less likely to trigger the force sensor (56) when the foot plate (28) is not in contact with the ground (52).

Figure 4:
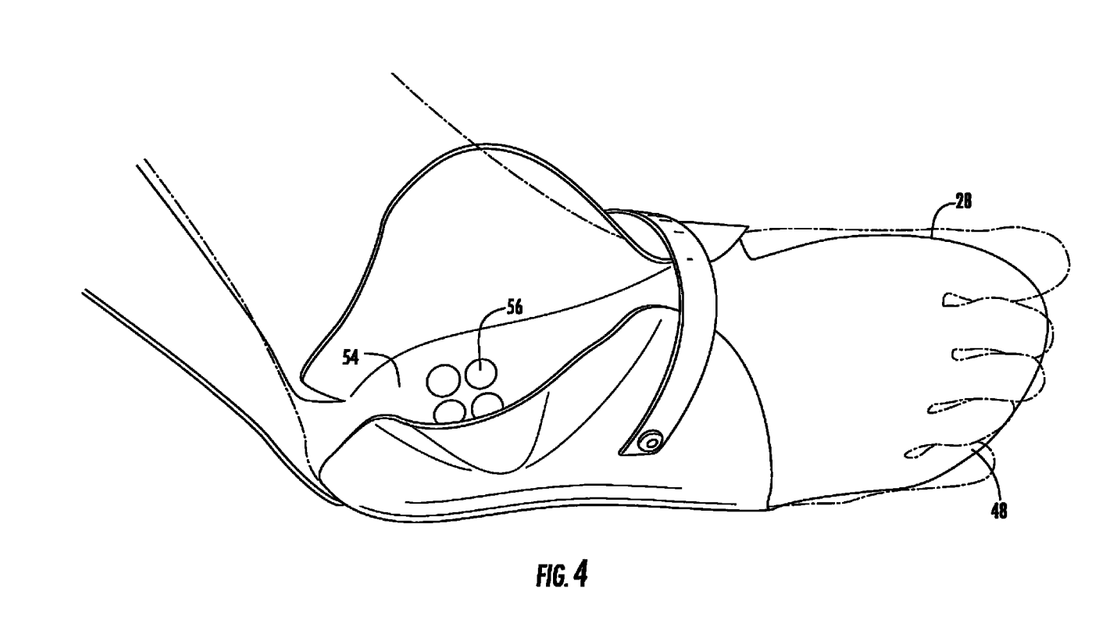
FIG. 4 is a top perspective view in partial phantom of the orthotic feedback system of FIG. 1.
Figure 5:
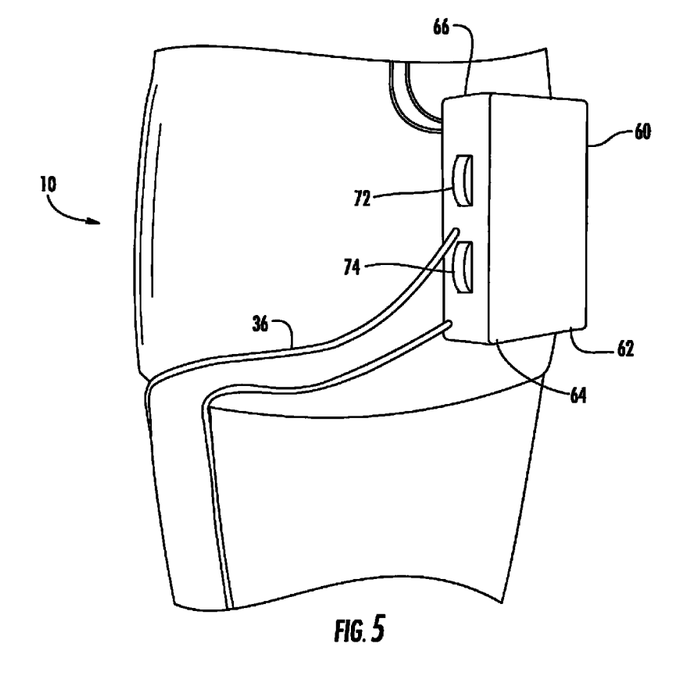
FIG. 5 is a side perspective view of the calf cuff of the orthotic feedback system of FIG. 1.

The force sensors (42) and (56) are coupled by wires (36) to a main control unit (60) having a central processing unit (62). (FIGS. 1, 3-4). The main control unit (60) may be of any suitable design but preferably includes a central processing unit (62) and a power source (64), such as a battery. The main control unit (60) may also be provided with an input jack (66), such as a USB port, to allow the main control unit (60) to be coupled to an external input device (68), such as a computer or a keyboard. A display (70) may be coupled to the main control unit (60), or may be coupled to the external input device (68), to indicate the status of the system (10) and to provide the user with input options.

Figure 6:
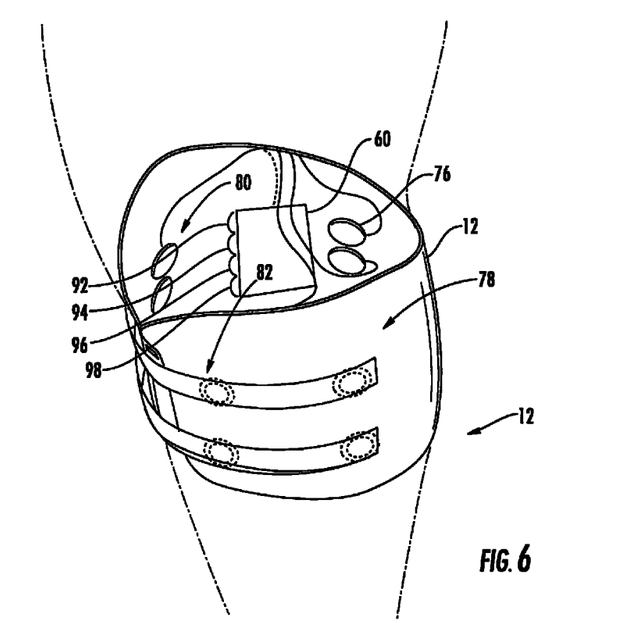
FIG. 6 is a top perspective view in partial phantom of the calf cuff of the orthotic feedback system of FIG. 1

If desired, the main control unit (60) may be coupled to the sensors (42) and (56) by potentiometers (72) and (74) which attenuate the signal traveling from the sensors (42) and (56) to the main control unit (60). (FIGS. 1, 3-5). As shown in FIGS. 1 and 6, four muscle stimulators are secured to the user's leg (14) with adhesive, in a manner such as that known in the art. Preferably, the muscle stimulators are transcutaneous electrode pads (76), (78), (80) and (82), but they may be any type of muscle stimulator known in the art. In the preferred embodiment, transcutaneous electrode pads (76), (78), (80) and (82), are transcutaneous electrical nerve stimulation adhesive pads, such as those known in the art to stimulate muscle groups. The two posterior transcutaneous electrode pads (76) and (78) are positioned on the posterior portion (84) of the user's calf (20) to stimulate the posterior calf muscle group (86). The anterior transcutaneous electrode pads (80) and (82) are secured to the anterior portion (88) of the calf (20) to stimulate the anterior calf muscle group (90). Alternatively, the transcutaneous electrode pads (76), (78), (80) and (82), may be secured to the calf cuff (18) of the orthosis (12).

Figure 7:
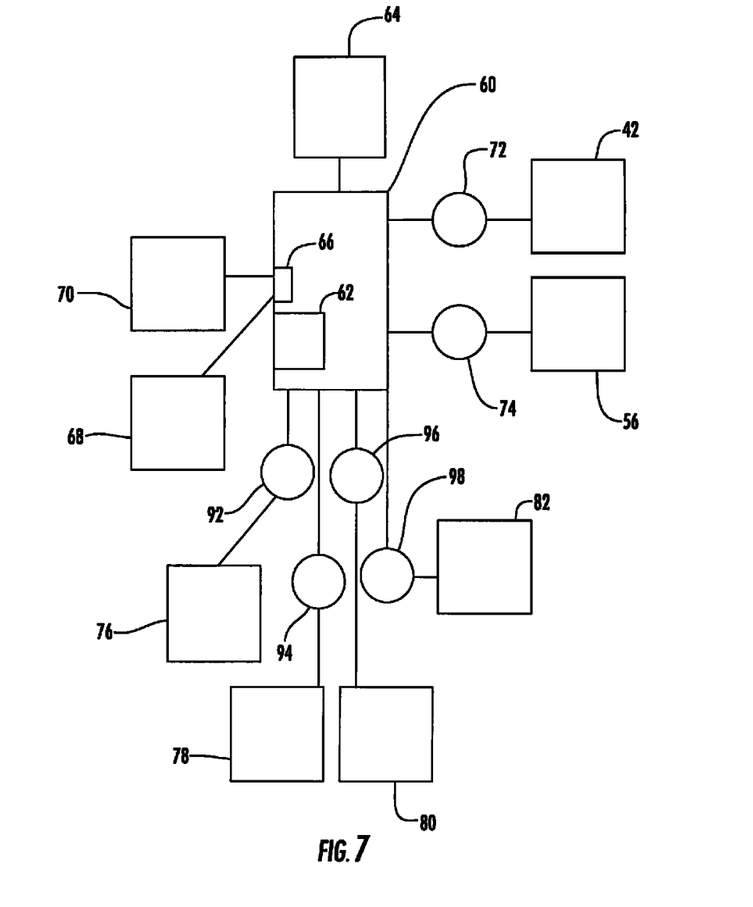
FIG. 7 is a block diagram showing components of the orthotic feedback system.

As shown in FIG. 6, the transcutaneous electrode pads (76), (78), (80) and (82), are wired to the main control unit (60). If desired, the transcutaneous electrode pads (76), (78), (80) and (82), may be coupled to the main control unit (60) via potentiometers (92), (94), (96) and (98) to attenuate the signal coming from the main control unit (60) to the transcutaneous electrode pads (76), (78), (80) and (82). (FIGS. 6-7).

Figure 8:
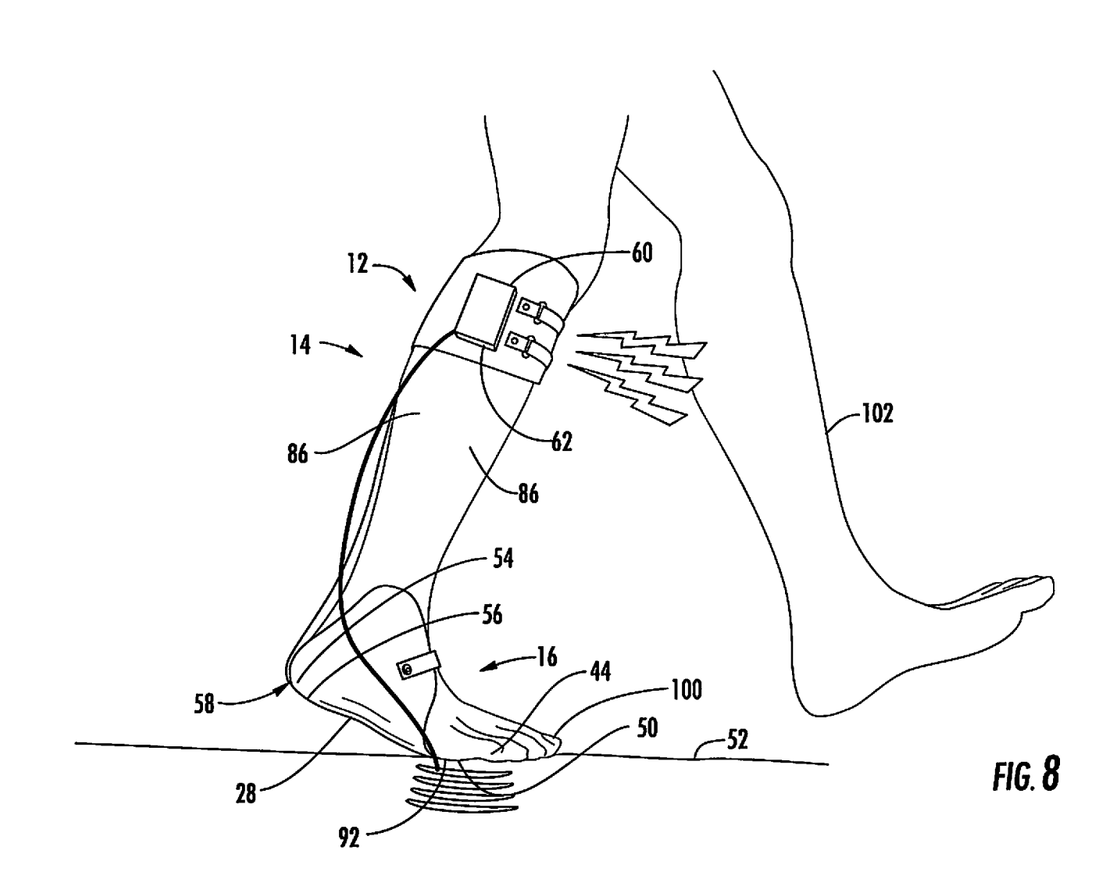
FIG. 8 is a side elevation of a user using the orthotic feedback system to push the user's leg forward.

To operate the system (10), the orthosis (12) is secured to the leg (14) and foot (16) of a user and the main control unit (60) is calibrated using the input device (68). The potentiometers (72), (74), (92), (94), (96) and (98) may be used to calibrate the main control unit (60) either alone, or in conjunction with the input device (68). The input device (68) may be used to store a set of instructions on the main control unit (60), to be executed by the central processing unit (62) to control firing of the transcutaneous electrode pads (76), (78), (80) and (82) in response to signals received from the sensors (42) and (56) at various stages of standing or walking As shown in FIG. 8, when the user begins to walk, the user lifts the leg (14) provided with the orthosis (12) so that the plantar surface (58) of the foot (16) is lifted off of the ground (52) before the metatarsal (50) of the foot (16) leaves the ground (52). In this position, the force sensor (42) under the metatarsal (50) of the foot (16) indicates pressure is still being applied to the ground (52) by the metatarsal (50) of the foot (16) while the force sensor (56) indicates that force is no longer being applied to the ground (52) by the plantar surface (58) of the foot (16). The force sensors (42) and (56) are preferably designed to indicate a graduated amplitude of impulse, depending upon the amount of compressive force placed upon the force sensors (42) and (56). The force sensors (42) and (56) also indicate compression on various areas of the sensors (42) and (56) and do not require a central force being applied to the sensors (42) and (56) to generate an impulse to the main control unit (60).

With the force sensor (54) indicating a decrease of compression on the plantar surface (54) of the foot plate (28), along with an increase in pressure to the force sensor (42) under the metatarsal (44) of the foot plate (28), the central processing unit (62) of the main control unit (60) uses a predetermined set of executable instructions to generate a signal that triggers the transcutaneous electrode pads (76), (78), (80) and (82) to stimulate plantar flexion firing of the posterior calf muscle group(s) (86), to extend the foot (16) and propel the user forward. (FIGS. 1, 6 and 8). As the user continues to move forward, a decrease of compression on the force sensor (42) under the metatarsal (44) of the foot plate (28) occurs. The decrease of compression alters the signal transmitted from the force sensor (42) to the main control unit (60) indicating that the user is transferring weight to the opposing leg. In response to the altered signal from the sensor (42), the central processing unit (62) uses the predetermined set of executable instructions to generate a signal that triggers the transcutaneous electrode pads (80) and (82) to stimulate dorsiflexion firing of the anterior calf muscle group(s) (90) on the anterior portion of the calf (20) to stimulate firing the dorsiflexors to raise the foot (16) to allow for clearance of the toes (100) as the user swings the foot (16) forward past the opposing leg.

Figure 9:
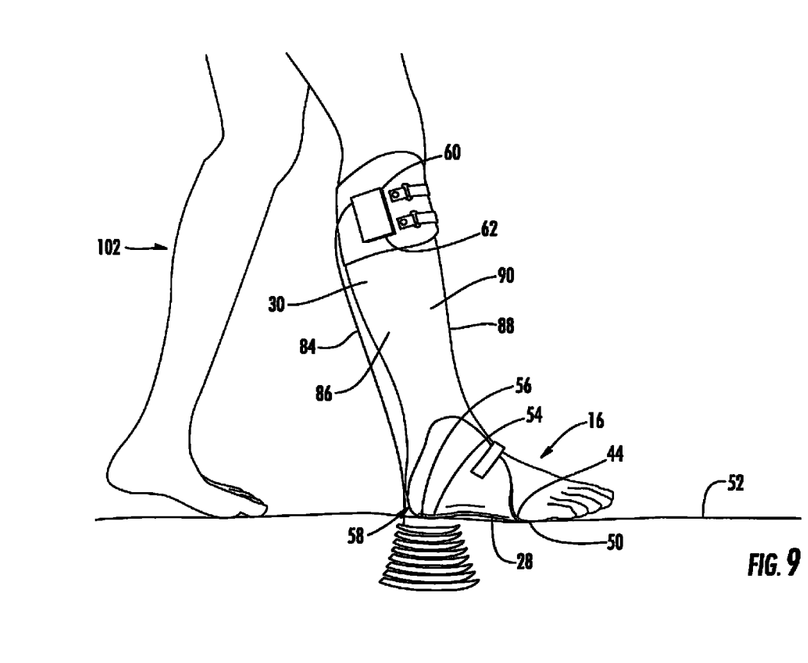
FIG. 9 is a side elevation of the orthotic feedback system shown facilitating landing on the heel of the user's foot.

As shown in FIG. 9, as the user moves the foot (16) forward and initiates placement of the plantar surface (58) of the foot (16) on the ground (52), the increasing compression of the force sensor (56) above the plantar surface (54) of the foot plate (28), causes the force sensor (56) to generate a signal and transmit that signal to the main control unit (60). In response to receipt of the signal from the force sensor (56), the central processing unit (62) of the main control unit (60) uses the predetermined set of executable instructions to generate a signal that triggers the transcutaneous electrode pads (76), (78), (80) and (82), to stimulate plantar flexion firing of the calf muscle group(s) (86) and/or (90), to generate plantar flexion of the foot (16) to extend the metatarsal (50) of the foot (16) toward the ground (52), until the force sensor (42) under the metatarsal area (44) of the foot plate (28) indicates that the metatarsal area (44) of the foot plate (28) is in contact with the ground (52). (FIGS. 3, 4, 6 and 9).

As the user continues walking, and begins to lift the opposing leg (102), the force sensors (42) and (56) send signals to the main control unit (60), indicating a transfer of pressure from the plantar area (58) of the foot (16) toward the metatarsal (44) of the foot (16). In response to receipt of these signals, the central processing unit (62) uses the predetermined set of executable instructions to generate a signal that triggers the transcutaneous electrode pads (76), (78), (80) and (82), to stimulate plantar flexion firing of the calf muscle group(s) (86) and/or (90), to compensate for the additional force being applied to the metatarsal (50) of the foot (16).

As the user continues to move the opposing leg (102) forward, past the leg (14) and into contact with the ground (52), the force sensors (42) and (56) continue to indicate an ongoing shift of pressures from the plantar surface (58) of the foot (16) to the metatarsal (50) of the foot (16), thereby causing the central processing unit (62) to use the predetermined set of executable instructions to generate a signal that triggers the transcutaneous electrode pads (76), (78), (80) and (82) to increase plantar flexion firing of the calf muscle group(s) (86) and/or (90), until the weight of the user has shifted to the opposing leg (102) and the force sensor (56) indicates a decreasing force being applied to the plantar surface (58) of the foot (16). (FIGS. 3, 4, 6, 8 and 9). The foregoing process then repeats, with the force sensors (42) and (56) indicating a decrease in pressure being applied to the plantar surface (58) of the foot (16), and an increase of pressure being applied to the metatarsal (50) of the foot (16) as the plantar surface (58) of the foot (16) begins to lift off the ground (52). At this point, the central processing unit (58) again uses the predetermined set of executable instructions to generate a signal that triggers the transcutaneous electrode pads (76), (78), (80) and (82) to stimulate plantar flexion firing of the calf muscle group(s) (86) and/or (90), to propel the user forward.

The input device (68) is connected to the main control unit (60) to retrieve the data relating to signals generated by the force sensors (42) and (56) and signals output to the transcutaneous electrode pads (76), (78), (80) and (82). The input device (68) uses the data to download a more efficient predetermine set of executable instructions to the main control unit (60) to tailor the output from the central processing unit (62) to the transcutaneous electrode pads (76), (78), (80) and (82), to better optimize the user's gait. Similarly, the input device (68) is used to optimize the predetermined set of executable instructions to the main control unit (60) to increase the efficiency with which the central processing unit (62) signals the transcutaneous electrode pads (76), (78), (80) and (82) to fire when the force sensors (42) and (56) indicate that the user is standing rather than walking Alternatively, or in addition, the potentiometers (66), (68), (86), (88), (90) and (92) may be adjusted to optimize the signals being provided from the central processing unit (62) to the transcutaneous electrode pads (76), (78), (80) and (82) to optimize the user's gait. As it is desirable for the central processing unit (62) to send varying signals to the transcutaneous electrode pads (76), (78), (80) and (82), depending upon whether the user is standing, walking slowing or walking quickly, use of an input device (68) to provide the predetermined set of executable instructions is preferable to merely adjusting the potentiometers (72), (72), (92), (94), (96) and (98), although adjustment of the potentiometers (72), (72), (92), (94), (96) and (98), may be used in conjunction with the predetermined set of executable instructions.

If desired, the predetermined set of executable instructions may include instructions to adjust the output from the central processing unit (62) to the transcutaneous electrode pads (76), (78), (80) and (82) as the user gains strength in the leg (14) and foot (16), so that less firing of the calf muscle group(s) (86) and (90) is required for ambulation. The gradual reduction of output signals to the transcutaneous electrode pads (76), (78), (80) and (82) increases the force required to be self-initiated by calf muscle group(s) (86) and (90). Through the foregoing, the system (10) aids in a faster return to normal ambulation, less injury to the user and maintenance of proper alignment of the foot (16) during recovery. This, in turn, may encourage return of muscle firing by the user to continue ambulation, which may lead to and even faster recovery.

From the foregoing, it will be appreciated that specific embodiments of the invention have been described herein for purposes of illustration, but that various modifications may be made without deviating from the spirit and scope of the invention. Accordingly, the invention is not limited except as by the appended claims. For example, the central processing unit (62) may cause the transcutaneous electrode pads (76), (78), (80) and (82) to fire in response to a predetermined set of signals from the force sensors (42) and (56), such as signals indicating the user has struck the ground (52) with the plantar surface (58) of the foot (16), then struck the ground (52) with the metatarsal (50) of the foot (16), and then released the pressure on the plantar surface (58) of the foot (16) to indicate the user is walking. Similarly, the central processing unit (62) may be programmed to not fire the transcutaneous electrode pads (76), (78), (80) and (82) until the force sensors (42) and (56) indicate a pressure greater than the user's weight, to indicate the pressure is associated with the user walking, as opposed to merely standing.

What is claimed is:
1. An orthotic device comprising:
    (a) an orthosis comprising:
        (i) a foot section; and
        (ii) a calf section coupled to the foot section;
    (b) a first gait position sensor coupled to the foot section wherein the first gait position sensor is positioned on the topside of the foot section;
    (c) a second gait position sensor coupled to the foot section wherein the second gait position sensor is positioned on the underside of the foot section;
    (d) a control unit coupled to the first gait position sensor and to the second gait position sensor;
    (e) a first muscle stimulator coupled to the control unit; and
    (f) a second muscle stimulator coupled to the control unit.
2. The orthotic device of claim 1, wherein the orthosis is resilient.
3. The orthotic device of claim 1, wherein the orthosis is of a construction designed to resiliently store energy during the compression phase of ambulation, and resiliently expend the stored energy during the extension phase of ambulation.
4. The orthotic device of claim 1, wherein the first gait position sensor is a force sensor.
5. The orthotic device of claim 1, wherein the first gait position sensor is a variable force sensor.
6. The orthotic device of claim 1, further comprising:
    (a) a third muscle stimulator coupled to the control unit; and
    (b) a fourth muscle stimulator coupled to the control unit.
7. The orthotic device of claim 6, wherein the first muscle stimulator is an anterior muscle stimulator, the second muscle stimulator is an anterior muscle stimulator, the third muscle stimulator is a posterior muscle stimulator, and the fourth muscle stimulator is a posterior muscle stimulator.

8. The orthotic device of claim 1, wherein the control unit comprises:
(a) a computer; and
(b) computer executable instructions.

9. A method of assisting the movement of a person, the method comprising:
(a) providing an orthotic device comprising:
   (i) an orthosis comprising:
      a. a foot section; and
      b. a calf section coupled to the foot section;
   (ii) a first gait position sensor coupled to the foot section;
   (iii) a first gait position sensor coupled to the foot section wherein the first gait position sensor is positioned on the topside of the foot section;
   (iv) second gait position sensor coupled to the foot section wherein the second gait position sensor is positioned on the underside of the foot section;
   (v) a first muscle stimulator coupled to the control unit;
   (vi) a second muscle stimulator coupled to the control unit;
(b) receiving a first gait signal from the first gait position sensor;
(c) in response to the step of receiving a first gait signal from the first gait position sensor, activating the first muscle stimulator;
(d) receiving a second gait signal from the second gait position sensor; and
(e) in response to the step of receiving a second gait signal from the second gait position sensor, actuating the second muscle stimulator.

10. The method of assisting the movement of a person of claim 9, wherein the first gait position sensor is positioned at the heel of the foot section.

11. The method of assisting the movement of a person of claim 10, wherein the second gait position sensor is positioned at the metatarsal of the foot section.

12. The method of assisting the movement of a person of claim 9, wherein the first gait position sensor is a force sensor.

13. The method of assisting the movement of a person of claim 9, wherein the first gait position sensor is a variable force sensor.

14. The method of assisting the movement of a person of claim 9, wherein the control unit comprises:
(a) a computer; and
(b) computer executable instructions.

15. A method of assisting the movement of a person, the method comprising:
(a) providing an orthotic device comprising:
   (i) an orthosis comprising:
      a. a foot section; and
      b. a calf section;
   (ii) a heel force sensor coupled to the top side of the foot section;
   (iii) a metatarsal force sensor coupled to the underside of the foot section;
   (iv) a control unit coupled to the heel force sensor and the metatarsal force sensor, the control unit comprising:
      a. a computer; and
      b. computer executable instructions;
   (v) a first muscle stimulator coupled to the control unit; and
   (vi) a second muscle stimulator coupled to the control unit;
(b) receiving a heel pressure signal from the heel force sensor;
(c) in response to the step of receiving the heel pressure signal, actuating the first muscle stimulator to stimulate plantar flexion;
(d) receiving a metatarsal pressure signal from the metatarsal force sensor; and
(e) in response to the step of receiving the metatarsal pressure signal, activating the second muscle stimulator to stimulate dorsiflexion.

* * * * *